United States Patent [19]
Paradis

[11] Patent Number: 5,921,264
[45] Date of Patent: Jul. 13, 1999

[54] SWABBABLE NEEDLELESS VALVE

[76] Inventor: Joseph R. Paradis, P.O. Box 22238, Hltn Hd Is., S.C. 29925

[21] Appl. No.: 08/920,040
[22] Filed: Aug. 28, 1997
[51] Int. Cl.⁶ .................................................. F16L 37/28
[52] U.S. Cl. ..................... 137/15; 251/149.1; 604/256; 604/905
[58] Field of Search ................. 251/149.1; 604/256, 604/905; 137/15

[56] References Cited

U.S. PATENT DOCUMENTS

| 5,269,771 | 12/1993 | Thomas et al. | 251/149.1 |
| 5,308,336 | 5/1994 | Hart et al. | 604/256 |
| 5,699,821 | 12/1997 | Paradis | 604/256 |

FOREIGN PATENT DOCUMENTS

| 3809127 | 4/1989 | Germany | 604/905 |

Primary Examiner—A. Michael Chambers
Attorney, Agent, or Firm—George E. Kersey, Esq.

[57] ABSTRACT

Apparatus and method wherein a housing with an outlet has a cap with an inlet and is affixed to the housing with a flexible flange that depends from the inlet of the cap to engage and circumferentially seal a fitting as it enters the inlet, the housing containing an interior seat for a flexible plug that extends within the housing to the cap for circumferentially sealing the inlet at the flexible flange, with the plug expanding from a circular to an elliptical cross section by the insertion of a Luer fitment into the inlet of the cap to a stop position within the housing, and the plug having an interior passageway extending from an open end to a head with a slit extending therethrough at the inlet.

13 Claims, 7 Drawing Sheets

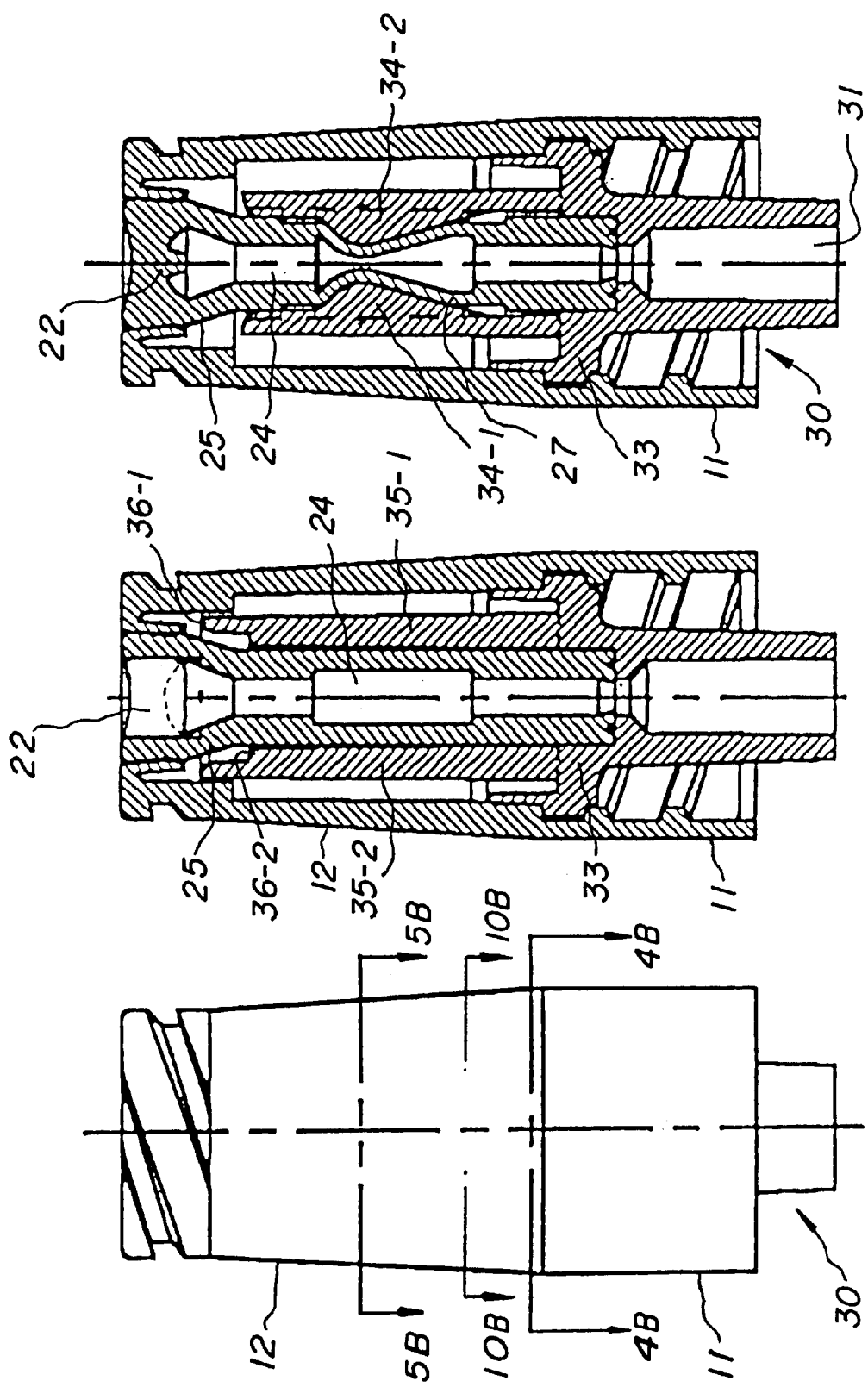

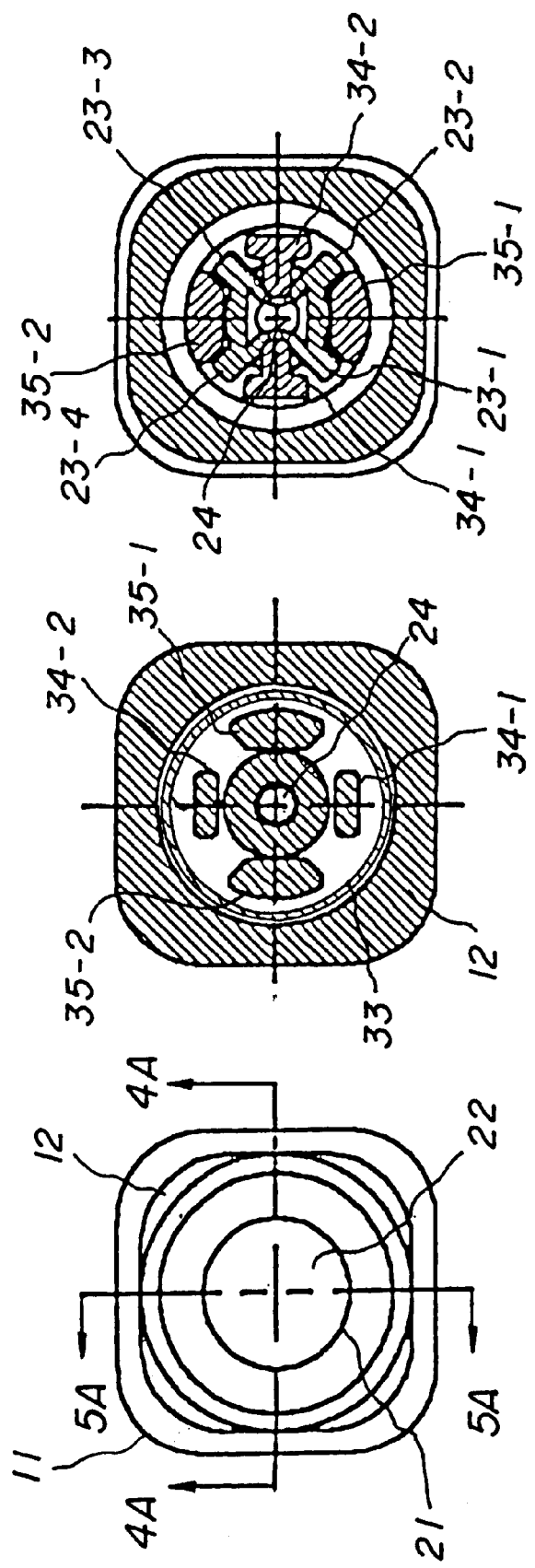

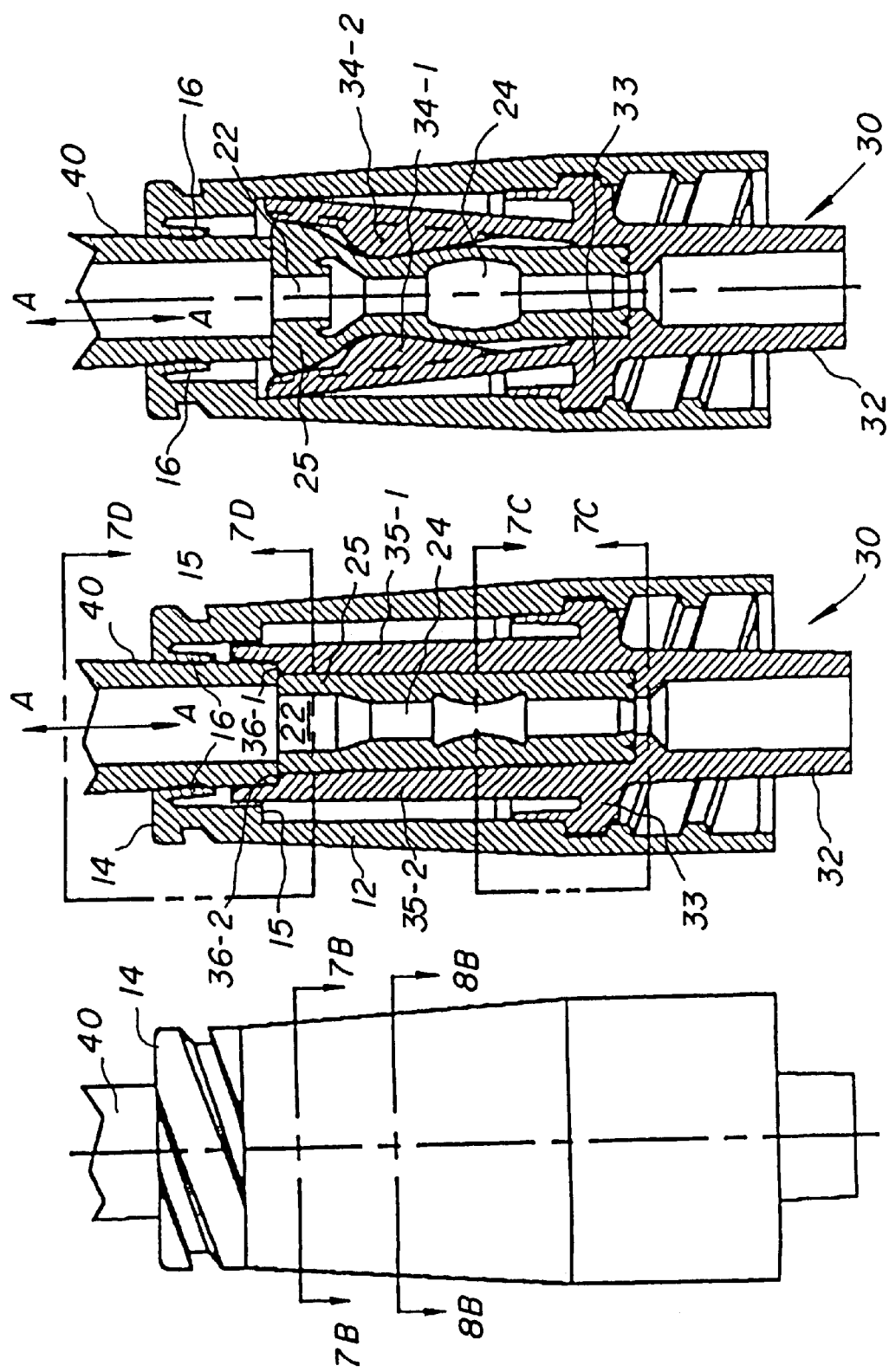

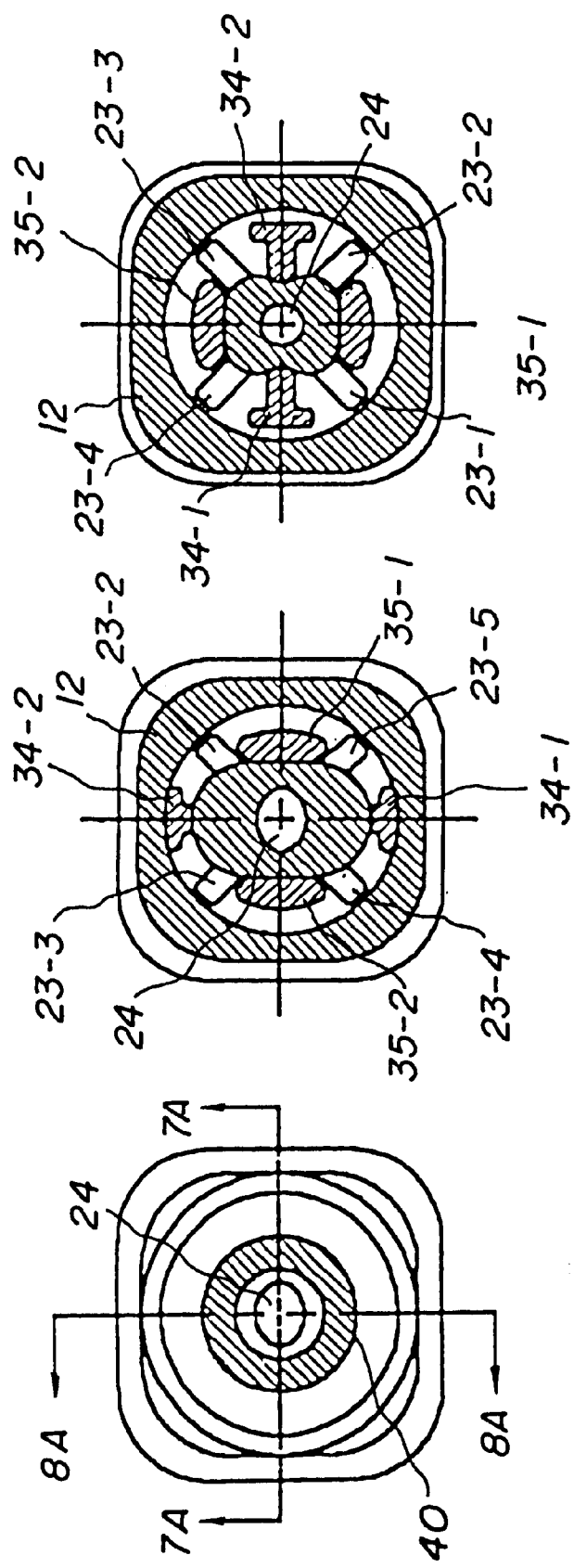

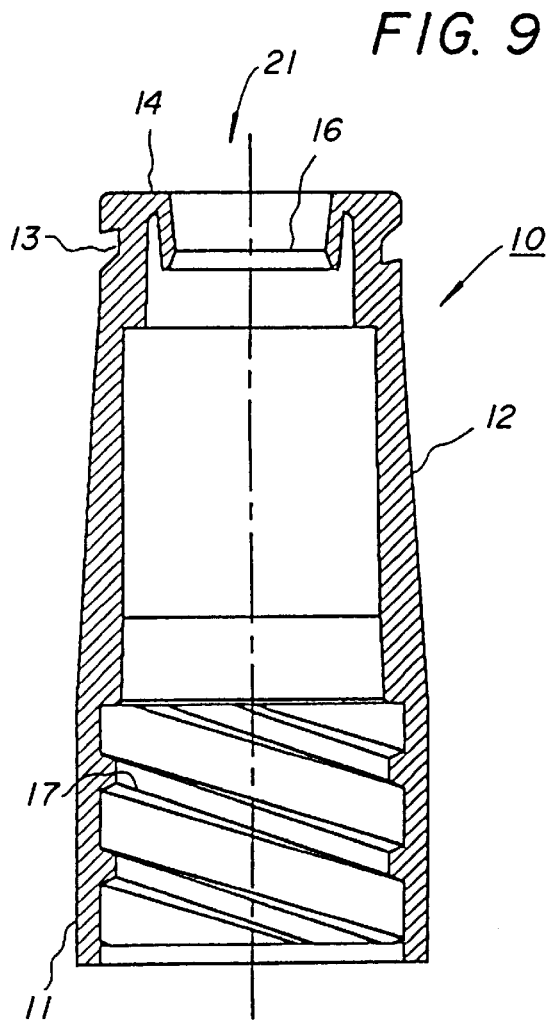
FIG. 9
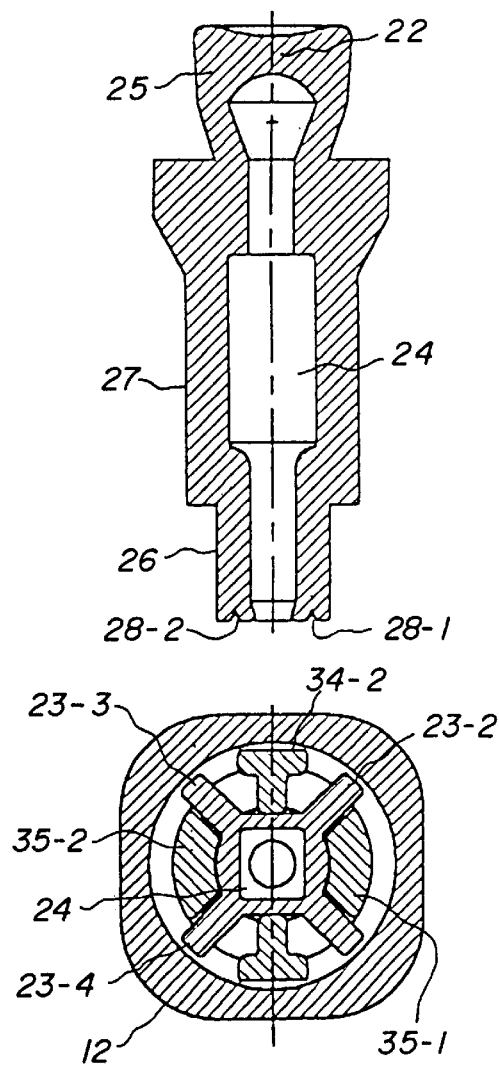
FIG. 10A
FIG. 10B

SWABBABLE NEEDLELESS VALVE

BACKGROUND OF THE INVENTION

This invention relates to flow control and, more particularly, to Luer activatable and swabbable valves for the needleless control of fluids.

A valve is a device that controls flow, for example, in two directions. Where fluids need to be introduced into, or removed from, the body, it is common practice to do so through a flow control valve connected to a catheter, which is a slender hollow tube inserted into a body passage or cavity for passing fluids. A catheter permits the control of fluid flow both into and out of the body passage.

For example, medication can be injected into a flow control valve connected to a catheter. In prior practice, medication from the syringe has been introduced using a needle, but this can be undesirable, since in modern medical practice, needle sticks are to be avoided. A number of attempts have been made to achieve the introduction of medication or the extraction of fluid without the need for using syringes with needles.

Illustrative examples of attempted needleless control of fluids are disclosed in Newgard et al., U.S. Pat. No. 5,064,416; Sivert, U.S. Pat. No. 4,915,687; Jackson, U.S. Pat. No. 4,429,856; Kilmarx, U.S. Pat. No. 3,352,531 and Faust et al. U.S. Pat. No. 5,116,021.

All of these illustrative arrangements have the objection that air borne and other pathogens can enter their inlets without being easily sterilized. While attempts have been made to maintain sterility by capping the inlets, the requirement of caps presents open passages during connection and additional complexity and expense. In addition, caps can become dislodged during storage and handling, rending the devices unusable or requiring special sterilization procedures.

Newgard '416 is typical in having a long inlet passage before there is access to a moveable member which is pierceable and controls flow by the extent to which a valving member can be dilated. Sivert, Johnson, Kilmarx and Faust are similarly objectionable.

Moreover, where valves are accessible by Luer fittings, instead of needles, the Luer fitting enters a long inlet passage before making contact with a moveable member that is unseated to permit fluid flow. Because of tolerance considerations, the inlet passage must be wide enough to accommodate the largest diameter Luer fitting. This means that for smaller diameter Luer fittings, within the tolerance specifications, there is a variable gap between the inlet wall of the valve and the Luer fitting being used to access the valve.

The result is a substantially large area for contamination by pathogens that cannot be neutralized by swabbing of the valve.

Accordingly, it is an object of the invention to overcome the problem of pathogen contamination that arises because of the need for valve inlets to accommodate a wide variety of Luer fitting diameters within the tolerance specifications that apply to such fittings.

Still another consideration is desire to operate flow control devices with low "cracking" pressures, i.e. the pressure at which a control member moves away from its seat. For such devices, it is desirable to use relatively thin diaphragms. Unfortunately, thin diaphragms pose problems of stability. The diaphragm may move slightly away from its central position and become lodged against a side wall, causing a problem of leakage.

The catheters used with flow control valves are of various types. One type includes a tubular member for the introduction of fluids into a blood channel which may be venous or arterial. Another type is a double-walled flexible tube which terminates at its outer end in two separate branches. One branch continues as an outer tube and terminates at its inner end in a inflatable portion.

The other branch continues as an inner tube with a through passage that extends to the inflatable portion of the outer tube. There are various other types of catheters as well.

With all types of catheters, it is desirable to be able to control the through flow of fluid using a suitable valve, which can be used in non-catheter applications as well.

Accordingly, it is another object of the invention to provide a miniature flow control valve which can be used without needles and is swabbable by being easily wiped with disinfectant across its inlet to eliminate contamination and pathogens. A related object is to allow the valve to be readily usable with devices, such as catheters, to control fluid flow while restricting operation by a patient or unauthorized personnel.

A further object of the invention is to provide a simple and expendable valve, which can be mass produced, readily assembled and provide ease of operation.

SUMMARY OF THE INVENTION

In accomplishing the foregoing and related objects, the miniature flow control valve of the invention is provided with "universal" Luer adaptation by having, depending from its inlet, a flexible seal that engages and seals the Luer fitting as it enters the inlet, regardless of size, for Luer fittings with the standard range of tolerances for such fittings. The flexible seal functions regardless of the Luer fitting diameter, and thus eliminates the possibility of pathogen contamination from the presence of any gap between the fitting and the interior of the valve before activation.

The invention also provides a tubular housing having centered at its inlet bore an annular seal plug that can be cleansed by swabbing, i.e., wiping, the inlet end before the annular seal plug is depressed by, for example, the blunt end of a syringe in order to open a slit in the plug and permit passage of fluid from the syringe through a longitudinal channel in the seal plug of the valve. The seal plug abuts an inwardly facing shoulder or valve seat of the flexible seal, and is held in its closed position by, for example, an insert into the housing against the seal plug, which is disengaged from the valve seat by an external member, such as the hollow blunt end of a syringe, or other male Luer adapter, containing fluid that is to be injected through the valve, for example, into a catheter or other medical, fluid-carrying entity.

In accordance with a broad aspect of the invention, the housing has opposed openings; a plug within the housing extending flush with an input opening of the housing, or slightly beyond it so that swabbing is easily accomplished; and an insert into the opening of the housing opposed to the input opening. The insert is desirably threaded into the opposed opening against the plug to hold it against the input. The insert can have Luer thread which engage complementary Luer threads extending within the opposed opening of the housing.

The housing input has an entrance and the sealing means can be substantially flush with the entrance. Where the entrance has a prescribed level, the sealing member can terminate at the prescribed level, or below it.

In a method of the invention the steps include: sealing an input by a pre-loaded force on a depressible seal plug with a slit at the input, with the plug held in position by an insert into a housing containing the plug; depressing the seal plug to open the slit and uncover a passageway through the plug connected to an output. As a result, the depression of the seal plug permits flow from the input to the output.

The method of the invention avoids the prior art methods which employ slotted seal members and require internal spikes that are sharp or blunt and are needed to penetrate the slotted seal member, requiring heavy opening forces that result in cutting of the seal member because of the need for seal member expansion within a restricted body volume. After several activations with such devices, the result is the introduction of undesirable contaminant particles in the fluid flow.

The seal plug of the invention is depressible from a position substantially flush with the entrance to the input. Where the entrance has a prescribed level, the seal plug is depressible from the prescribed level, or from below the prescribed level where is desirable to provide a locator for the instrumentality, such as a syringe, by which the seal plug is depressed.

In a method of manufacturing a swabbable valve the steps include: (a) providing a housing having opposed openings including an input opening; (b) sealing the input by a member engaging the housing at the input opening and having an internal longitudinal channel terminating at a slit input end; and (c) holding the sealing member at the input opening of the housing by an insert into the opening of the housing opposed to the input opening. The position of the input end of the sealing member permits swabbing before depression to allow fluid flow to and through the insert.

A miniature valve in accordance with the invention includes a tubular housing having opposed openings, including an inlet opening at a level surrounded by an exterior surface; a bore extending from the exterior surface into the housing; a flexible seal member centered at the inlet at the level of the exterior surface, with the seal member having an internal channel extending to an outlet of an insert by which the seal member is held in the housing, with the annular seal plug being depressible to open its end and permit flow through its internal passageway.

Swabbing is facilitated where the annular seal plug is flush with the inlet.

The apparatus of the invention encompasses means having an exterior surface at a level containing an inlet; depressible means centered in the inlet at the level of the exterior surface and having a passageway for communicating with the inlet and extending to an interior channel for communicating with an outlet; whereby the exterior surface and the depressible member can be swabbed to reduce contamination and pathogens before the depressible member is depressed. Moreover, the flexible input seal of the invention allows the accommodation of a wide range of Luer fitments, regardless of tolerance variations within the applicable manufacturing limits, to prevent the entrance of pathogens and other contaminants into the fluid stream once activation has taken place.

The housing of the invention has an interior with a bore extending from an inlet into the housing; a depressible member is centered in the housing and included in any hypothetical extension of the inlet surface; the depressible member has exterior slit and an interior channel extending to an outlet member that holds the depressible member within the housing. The depressible member is annular and the interior of the housing seals the inlet.

In accordance with still another aspect, the invention provides a housing having opposed openings, including an input; a sealing plug within the housing extending axially from an output to the input; with the plug having a passageway thereinto connected to the output. The sealing means of the housing can be a flexible circular seal having an axially extending wall, which engages the plug.

The sealing means of the housing can include a member surrounding the plug, and the axially extending wall can engage the member by being included in a housing that surrounds the member below the input.

An actuator can depress the sealing member and pressure applied through the actuator can open a passageway to the outlet.

The method can further include the step of sealing the input, for example, by a Luer insert or the seal plug, by a flexible circular seal having an axially extending wall, and the seal plug can be engaged by the axially extending wall. The axially extending wall can be included in a housing surrounding the seal plug at the input inlet.

The method can further include the step of axially extending the interior wall to form the frustum of a hollow cone, and an actuator can be applied to depress the sealing member and cause pressure applied through the actuator to open a passageway to the outlet.

The method also can include the steps of sealing an input by a depressible member extending to the input; and depressing the member in sealing engagement therewith. Pressure can be applied at the input to unseal the engagement of the member.

DESCRIPTION OF THE DRAWINGS

Other aspects of the invention will become apparent after considering several illustrative embodiments taken in conjunction with the drawings in which:

FIG. 3A is a further plan view of the illustrative embodiment of FIG. 1A, taking the form of a swabbable, needleless valve;

FIG. 3B is an end view of the embodiment of FIG. 1A showing a horizontally-disposed slit in the depressible seal plug of the invention;

FIG. 4A is a sectional view of the valve of FIGS. 3A and 3B taken along the lines C—C of FIG. 3B;

FIG. 4B is a sectional view of the valve of FIGS. 3A and 3B taken along the lines F—F of FIG. 3A;

FIG. 5A is a sectional view of the valve of FIGS. 3A and 3B taken along the lines D—D of FIG. 3B;

FIG. 5B is a sectional view of the valve of FIGS. 3A and 3B taken along the lines E—E of FIG. 3A;

FIG. 6A is a plan view of an illustrative embodiment of the invention, taking the form of a swabbable, needleless valve, being activated by the tip of a Luer fitting;

FIG. 6B is an end view of the embodiment of FIG. 6A showing the action of the Luer tip of FIG. 6A in opening the horizontally-disposed slit in the depressible seal plug of the invention;

FIG. 7A is a sectional view of the valve of FIGS. 6A and 6B taken along the lines G—G of FIG. 6B;

FIG. 7B is a sectional view of the valve of FIGS. 6A and 6B taken along the lines I—I of FIG. 6A;

FIG. 8A is a sectional view of the valve of FIGS. 6A and 6B taken along the lines H—H of FIG. 6B;

FIG. 8B is a sectional view of the valve of FIGS. 6A and 6B taken along the lines J—J of FIG. 6A;

FIG. 9 is a cross-sectional view of an illustrative housing for the valve of the invention;

FIG. 10A is a further view of the seal plug of the invention; and

FIG. 10B is a sectional view of the valve of FIG. 3A taken along the lines M—M to illustrate further details of the seal plug in its intermediated region.

DETAILED DESCRIPTION

Figure 1B:
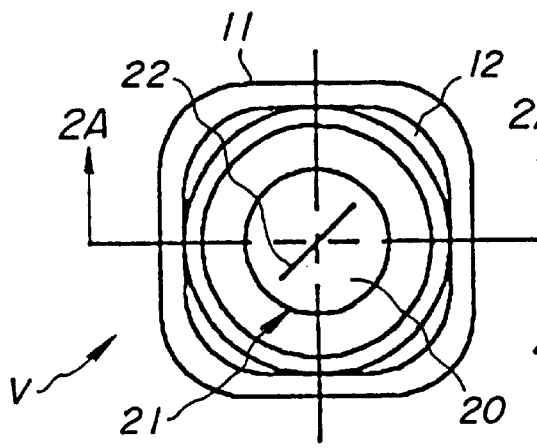
FIG. 1B is an end view of the embodiment of FIG. 1A showing a diagonally-disposed slit in the depressible seal plug of the invention.
Figure 1A:
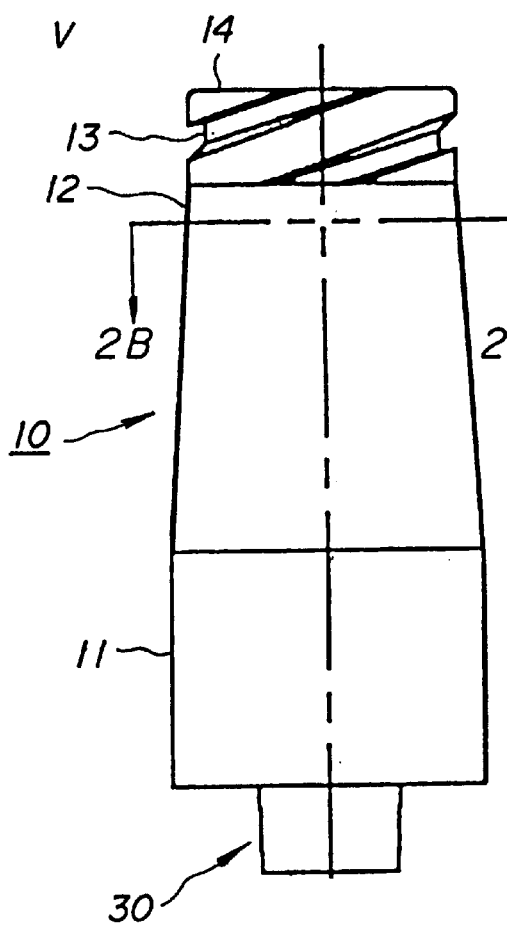
FIG. 1A is a plan view of an illustrative embodiment of the invention, taking the form of a swabbable, needleless valve.

With reference to the drawings, an embodiment of the invention is provided by the swabbable needleless valve V of FIG. 1A with a single-part tubular housing 10. The housing 10 contains an annular seal plug 20 that is centered in the bore of the housing 10 and contains an axial slot 22 shown in FIG. 1B that extends into a channel 24 of the plug 20 as shown in FIG. 2A.

The housing 10 is illustratively formed with a curved rectangular base 11 joined to a top 14 by a tapered intermediate region 12. Before insertion of the plug 20, the housing has opposed opening, one at the top 14 and the other at the unconnected end of the base 11.

Figure 2B:
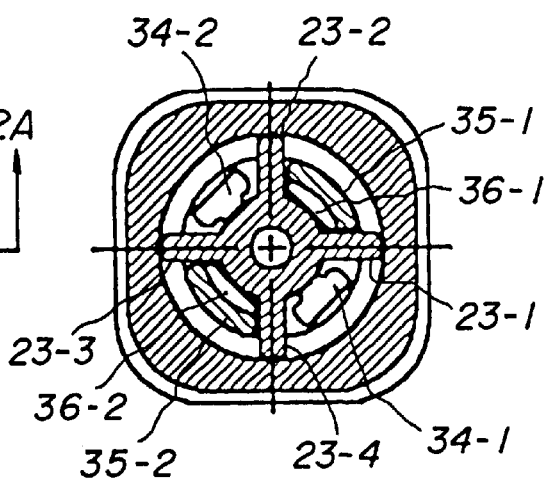
FIG. 2B is a sectional view of the valve of FIGS. 1A and 1B taken along the lines B—B of FIG. 1A.
Figure 2A:
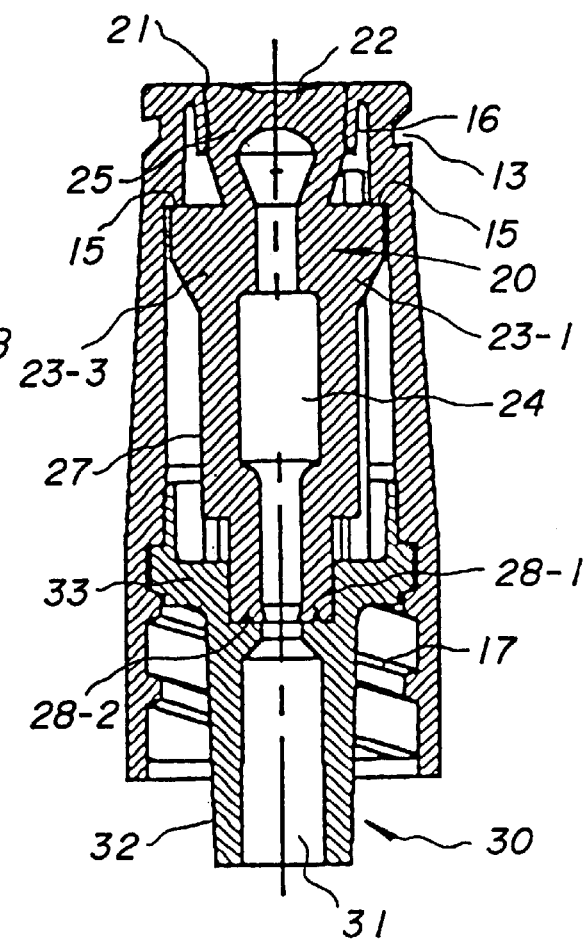
FIG. 2A is a sectional view of the valve of FIGS. 1A and 1B taken along the lines A—A of FIG. 1B.

As indicated in FIG. 2A, the upper portion or head 25 of the seal plug 20, below the inlet 21 of the housing 10, slidably engages an internal pendant flange 16 at the upper end of the housing 10, while the intermediate portion 27 of the sealing member 20 surrounds an enlarged region of a channel 24 that extends from the slit 22. The intermediate portion 27 is partially spaced from the interior wall of the housing 10, and extends into contact with an internal stop 15 of the housing 10. The region of the channel 24 below the slit 22 is dome shaped with a diagonal wall that extends to a reduced diameter portion of the channel 24 that connects to the enlarged intermediate, which extends to a further open-ended region of reduced diameter in the base 26 of the plug 20.

In addition to its action against the upper portion of the seal plug 20, the circular flexible flange 16 allows the valve V to accommodate a wide variety of syringes and male Luer fitments, as illustrated below in conjunction with FIGS. 6A–8B, since the circular flexible flange 16 is biased inwardly towards the bore of the housing 10 and expands outwardly depending upon the diameter of the fitment or syringe that is inserted into the inlet 21.

The sealing member 20 is held in its operative sealing position against the circular flange 16 by an insert 30 threaded into the base 11 of the housing 10, but other structures may be employed as well. The insert 30 includes a cup portion 33 that engages the base 26 of the plug 20, surrounding a male Luer prong 32 that forms an outlet 31 below the base 11 of the housing 10. Accordingly, the sealing member 20, desirably elastomeric, may be elongated beyond the length indicated and subjected to compressive force to produce the compression grooves 28-1 and 28-2 in the base 26 of the plug 20 causing a positive fluid seal.

Extending upwardly from the cup 33 of the insert 30 are cantilever fingers 34-1 and 34-2 as shown in FIG. 2B. Also extending upwardly from the cup 33 are support fingers 35-1 and 35-2, also shown in FIG. 2B. The cantilever fingers 34-1 and 34-2 produce flexure of the plug 20 between longitudinally extending plug ribs 23-1 and 23-4 for insert finger 34-1 and between longitudinally extending plug ribs 23-2 and 23-3 for insert finger 34-2. The longitudinally extending insert fingers 35-1 and 35-2 provide support for the plug 20. Like the tubular housing 10, the insert 30 and its appendages can be formed of a moldable plastic.

In FIG. 3B the diagonally disposed slit 22 of the embodiment in FIG. 1A has been horizontally disposed so that other aspects of the swabbable, needleless valve of the invention are illustrated.

Thus in the sectional views of FIGS. 4A and 5B the insert fingers 35-1 and 35-2 are shown in their support position adjoining the length of the plug 20, while in the sectional views of FIGS. 4B and 5A the cantilever fingers 34-1 and 34-2 are shown flexing the midsection 27 of the plug 20.

Operation of the valve V is illustrated in FIGS. 6A through 8B using an external member, such as the Luer tip 40 of a syringe. When the valve V is to be operated, the external member 40 is brought into contact with the sealing member 20 at the inlet 21. The sealing member 20 is pushed or forced inwardly from its normal seating position encircled by the internal flange 16. When forced inwardly as shown in FIG. 7A, the top of the sealing member 20 is depressed below the internal flange 16 to the notch positions 36-1 and 36-2 of the insert fingers 35-1 and 35-2 to open the transverse slit 22 and thus establish open communication for fluid through the central channel 24 of the bore and the outlet 31 of the insert 30 in either direction, e.g. inwardly or outwardly of the valve V, as indicated by the double-headed arrows A in FIGS. 7A and 8A.

Details of the circular flexible flange 16 are shown in the enlarged cross section of FIG. 9 which ensures closure of the inlet to prevent any outflow. In addition, the flexibility of the walls for the flange 16 allow the valve V to accommodate a wide variety of Luer fitments and syringes since the inlet 21 can have a diameter that will receive the largest diameter fitment while the flange 16 assures closure around the smallest diameter fitment below the inlet 21.

In the sectional view of FIG. 10B for the valve of FIG. 3A, taken along the lines M—M, the seal plug 20 in its intermediated region has a channel 24 of square cross section, with the insert cantilever fingers 34-1 and 34-2 positioned just before flexure of the plug 20, as shown in FIG. 2B.

The valve V of the invention has a wide variety of uses, besides with catheters and the like. One such use is the incorporation into a "Y" site that can be used, for example, in an IV (IntraVenous) procedure where the inlet branch of the Y site is connected to a container of solution that is fed through an outlet branch to a patient. The side branch of the site can be used to inject medication into the patient. In prior practice the side branch channel would be accessed through a needle actuated valve, but in the interest of avoiding needle sticks, needleless valves have been substituted. However, as noted above, the typical needleless valve has a long inlet channel in which contaminants and pathogens can accumulate.

When the valves of the invention are used, they are swabbable by being wiped with a disinfectant so that when a Luer fitting is brought into contact with the sealing member 20, the desired medicament can be infused with reduced chance of contamination and no need to used a needle mounted syringe to make the injection.

In a further use of the invention, a valve 60 of the invention is incorporated into a catheter, that also can be used, for example, in an IV (IntraVenous) procedure. In prior practice the catheter would be accessed through a needle actuated valve, but in the interest of avoiding needle sticks, needleless valves have been substituted. However, as noted above, the typical needleless valve has a long inlet channel in which contaminants and pathogens can accumulate.

Figure 7C:
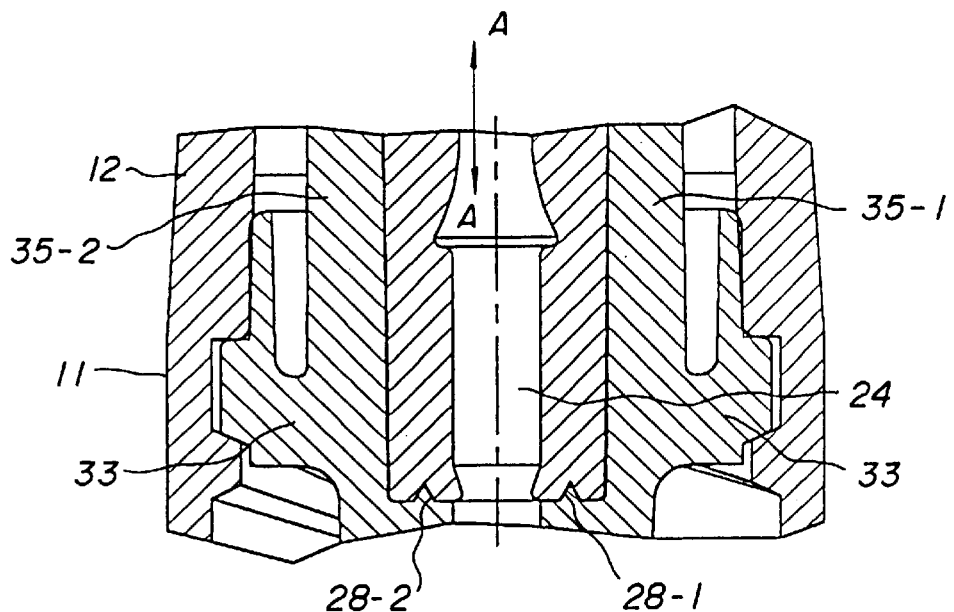
FIG. 7C is an enlargement of the valve of FIG. 7A taken along the lines K—K of FIG. 7A.
Figure 7D:
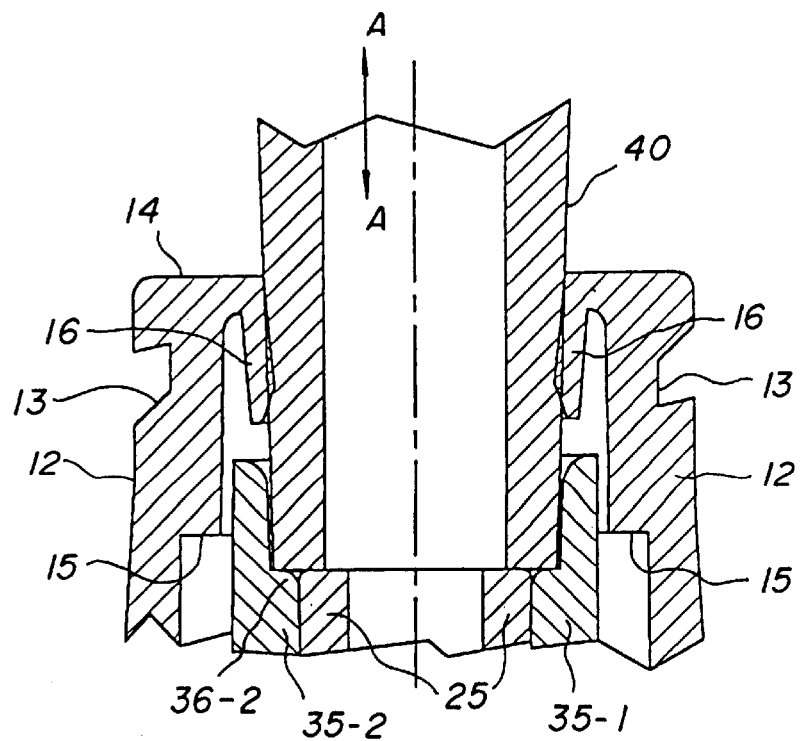
FIG. 7D is an enlargement of the valve of FIG. 7A taken along the lines L—L of FIG. 7A.

It is to be noted that when a fitment, such as a Luer taper, is inserted into the valve, the flow channel is expanded in FIGS. 7A and 8A, and there is an increase in cross-section. When the fitment is withdrawn, there is a decrease in cross-section in FIGS. 4A and 5A. The result is the application of flushing pressure against back-flow when the fitment is withdrawn.

While preferred embodiments have been shown and described, it is to be understood that changes in details of construction and method from what has been illustrated may be made without departing from the spirit and scope of the invention as defined by the appended claims.

What is claimed:

1. The method of adapting a valve to adapters having various tolerances comprising the steps of:
   (a) providing an input with a continuous internal flexible flange having an axially extending wall;
   (b) inserting said actuator against said flange which sealingly accommodates tolerance variations in the inserted portion of said actuator by virtue of said internally flexible wall; and
   (c) engaging a flexible plug completely sealing said inlet at said flexible flange and held thereagainst by an insert with a plurality of longitudinal arms.

2. The method as defined in claim 1 including the step of providing a channel that extends from said input to permit flow therethrough and has a cross-sectional opening that increases when said actuator is inserted, with said cross-sectional opening decreasing when said actuator is withdrawn to apply flushing pressure against back flow.

3. Apparatus comprising
   a housing having an inlet opening; and
   a continuous and flexible flange depending from said inlet to engage and circumferentially seal a fitting as it enters said inlet opening;
   wherein said housing has another opening opposed to said inlet opening receiving a flexible plug for completely sealing said inlet opening at said flexible flange and held thereagainst by an insert, with a plurality of longitudinal arms, into said another opening.

4. Apparatus as defined in claim 3 wherein said plug has a passageway therein extending from an open end to a head at the entrance of said inlet opening with a slit extending therethrough.

5. Apparatus as defined in claim 3 wherein said flexible flange comprises a circular seal having an axially extending circumferential wall.

6. Apparatus as defined in claim 5 wherein said axially extending wall is included in a housing that surrounds said plug below said inlet opening.

7. Apparatus as defined in claim 5 wherein said axially extending wall is the frustum of a hollow cone.

8. Apparatus as defined in claim 3 wherein said insert is threaded into said housing at said another opening.

9. Apparatus as defined in claim 3 wherein an actuator is used to depress said plug and pressure applied through said actuator opens a passageway to said insert.

10. Apparatus as defined in claim 3 wherein said plug has a plurality of longitudinal ribs.

11. Apparatus as defined in claim 3 wherein at least one of said longitudinal arms is a cantilever finger.

12. Apparatus as defined in claim 3 wherein at least one of said longitudinal arms is a support finger.

13. Apparatus as defined in claim 3 wherein said housing has an internal stop for fixing the position of said plug relative to said inlet.

* * * * *